(12) United States Patent
Nakamura et al.

(10) Patent No.: US 9,394,235 B2
(45) Date of Patent: Jul. 19, 2016

(54) OPTICAL RESOLUTION METHODS FOR BICYCLIC COMPOUNDS USING ENZYMES

(71) Applicant: Daiichi Sankyo Company, Limited, Tokyo (JP)

(72) Inventors: Yoshitaka Nakamura, Kanagawa (JP); Yukito Furuya, Kanagawa (JP); Kousei Shimada, Tokyo (JP); Yoshiyuki Onishi, Tokyo (JP)

(73) Assignee: DAIICHI SANKYO COMPANY, LIMITED, Tokyo (JP)

( * ) Notice: Subject to any disclaimer, the term of this patent is extended or adjusted under 35 U.S.C. 154(b) by 0 days.

(21) Appl. No.: 14/511,386

(22) Filed: Oct. 10, 2014

(65) Prior Publication Data

US 2015/0038738 A1    Feb. 5, 2015

Related U.S. Application Data

(63) Continuation of application No. PCT/JP2013/060597, filed on Apr. 8, 2013.

(30) Foreign Application Priority Data

Apr. 10, 2012 (JP) ................. 2012-089481

(51) Int. Cl.
| | |
|---|---|
| *C07C 227/22* | (2006.01) |
| *C07C 227/12* | (2006.01) |
| *C07C 229/32* | (2006.01) |
| *C07C 45/85* | (2006.01) |
| *C12P 41/00* | (2006.01) |
| *C12P 7/02* | (2006.01) |
| *C12P 7/26* | (2006.01) |
| *C07C 201/12* | (2006.01) |
| *C07C 227/04* | (2006.01) |
| *C07C 227/18* | (2006.01) |
| *C07B 57/00* | (2006.01) |

(52) U.S. Cl.
CPC ............. *C07C 227/22* (2013.01); *C07C 45/85* (2013.01); *C07C 201/12* (2013.01); *C07C 227/04* (2013.01); *C07C 227/12* (2013.01); *C07C 227/18* (2013.01); *C07C 229/32* (2013.01); *C12P 7/02* (2013.01); *C12P 7/26* (2013.01); *C12P 41/002* (2013.01); *C07B 57/00* (2013.01); *C07C 2102/20* (2013.01)

(58) Field of Classification Search
CPC ....................................................... C07B 57/00
See application file for complete search history.

(56) References Cited

U.S. PATENT DOCUMENTS

| | | | |
|---|---|---|---|
| 7,947,738 B2 | 5/2011 | Shimada et al. | |
| 8,324,425 B2 | 12/2012 | Kitagawa et al. | |
| 2003/0078300 A1 | 4/2003 | Blakemore et al. | |
| 2003/0220397 A1 | 11/2003 | Bryans et al. | |
| 2004/0152779 A1 | 8/2004 | Bryans et al. | |
| 2006/0154929 A1 | 7/2006 | Anker et al. | |
| 2010/0249229 A1 | 9/2010 | Shimada et al. | |
| 2014/0094623 A1* | 4/2014 | Nakamura ............ | C07C 45/515 562/501 |
| 2014/0094624 A1 | 4/2014 | Nakamura et al. | |

FOREIGN PATENT DOCUMENTS

| | | |
|---|---|---|
| JP | 60-169434 A | 9/1985 |
| WO | WO 2009/041453 A1 | 4/2009 |
| WO | WO 2010/084798 A1 | 7/2010 |
| WO | WO 2010/110361 A1 | 9/2010 |
| WO | WO 2012/169474 A1 | 12/2012 |

OTHER PUBLICATIONS

Bryans et al., "Identification of Novel Ligands for the Gabapentin Binding Site on the $\alpha_2\delta$ Subunit of a Calcium Channel and Their Evaluation as Anticonvulsant Agents," *J. Med. Chem.*, (1998), 41:1838-1845.
Gee et al., "The Novel Anticonvulsant Drug, Gabapentin (Neurontin), Binds to the $\alpha_2\delta$ Subunit of a Calcium Channel," *J. Biol. Chem.*, (1996), 271(10):5768-5776.
Marotta et al., "A New, Effective Route to Methyl Substituted 3,3a,4,6a-Tetrahydro-2*H*-cyclopenta[*b*]furan-2-ones," *Tetrahedron Letters*, (1994) 35(18):2949-2950.
International Search Report issued Jul. 2, 2013 in PCT Application No. PCT/JP2013/060597, 2 pages.
Bortolini et al., "An Easy Approach to the Synthesis of Optically Active *vic*-Diols: A New Single-Enzyme System," *J. Org. Chem.*, (1997), 62:1854-1856.

\* cited by examiner

*Primary Examiner* — Bin Shen
(74) *Attorney, Agent, or Firm* — Dorsey & Whitney LLP

(57) ABSTRACT

An object of the present invention is to efficiently produce an optically active bicyclic compound. The optically active bicyclic compound is efficiently produced using an enzyme.

8 Claims, No Drawings

OPTICAL RESOLUTION METHODS FOR BICYCLIC COMPOUNDS USING ENZYMES

This application claims the benefit under 35 U.S.C. §111 (a) as a continuation application of International Application No. PCT/JP2013/060597, filed Apr. 8, 2013, entitled "Optical Resolution Method for Bicyclic Compound Using Enzyme," which claims priority to Japanese Patent Application No. 2012-089481, filed Apr. 10, 2012.

TECHNICAL FIELD

The present invention relates to a method for producing an optically active bicyclic γ-amino acid derivative or a pharmacologically acceptable salt thereof, particularly, a compound having activity as an $\alpha_2\delta$ ligand and an intermediate thereof.

BACKGROUND ART

Compounds that exhibit high-affinity binding to voltage-dependent calcium channel subunit $\alpha_2\delta$ have been shown to be effective for treating, for example, neuropathic pain (see e.g., Non-patent Literatures 1 and 2).

Several types of $\alpha_2\delta$ ligands are currently known as therapeutic drugs for neuropathic pain. Examples of $\alpha_2\delta$ ligands include gabapentine and pregabalin. $\alpha_2\delta$ ligands such as these compounds are useful for treating epilepsy and neuropathic pain or the like (e.g., Patent Literature 1). Other compounds are disclosed in, for example, Patent Literatures 2, 3, and 4.

Also, the present applicant has previously reported an $\alpha_2\delta$ ligand and a method for producing the same in Patent Literatures 5 and 6.

CITATION LIST

Patent Literature

Patent Literature 1: US 2006/154929
Patent Literature 2: US 2003/220397
Patent Literature 3: US 2004/152779
Patent Literature 4: US 2003/78300
Patent Literature 5: US 2010/249229
Patent Literature 6: WO 2010/110361

Non Patent Literature

Non Patent Literature 1: J Biol. Chem. 271 (10): 5768-5776, 1996
Non Patent Literature 2: J Med. Chem. 41: 1838-1845, 1998

SUMMARY OF INVENTION

Technical Problem

An object of the present invention is to provide a method for producing an optically active bicyclic γ-amino acid derivative or a pharmacologically acceptable salt thereof, particularly, a compound having activity as an $\alpha_2\delta$ ligand and an intermediate thereof.

Patent Literatures 5 and 6 have reported a method for producing compound 6 as described in Scheme 1.

Focusing on a stereocontrol method for an asymmetric carbon as a method for producing compound 6, the present inventors have continued diligent studies to develop an efficient method therefor. In the previous production method, optical resolution is performed in a step (Step 4) immediately prior to the final step. The present inventors, however, have hypothesized that a more efficient production method would be established by carrying out the optical resolution in an earlier step.

Specifically, a technical problem to be solved by the present invention is to develop a production method which involves preparing an intermediate of compound 6 as an optically active compound in an earlier step in the production of compound 6. The present inventors have continued diligent studies to solve this problem and consequently completed the present invention by solving the problem.

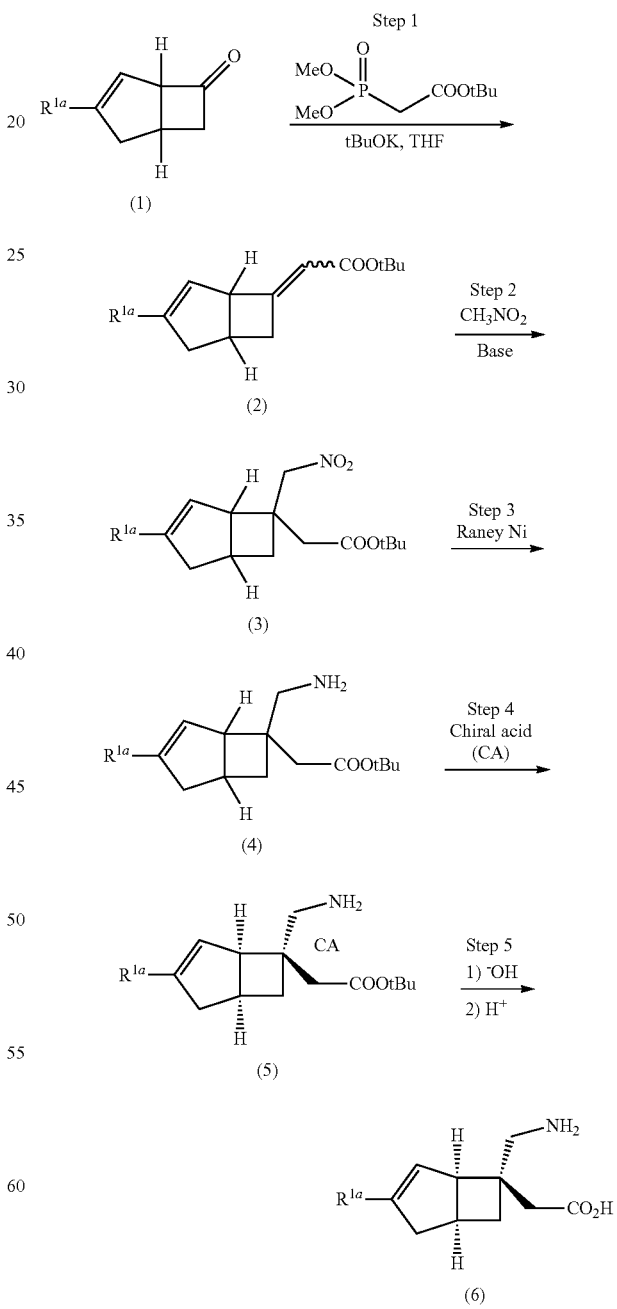

Scheme 1

[Formula 1]

wherein the substituent is defined as follows: $R^{1a}$: a hydrogen atom or a C1-C6 alkyl group.

3
Solution to Problem

The present invention will be described below.

[1] A method for producing a compound represented by the general formula (I) or a compound represented by the general formula (II):

[Formula 2]

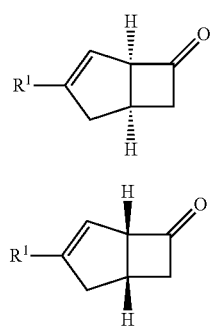

the method comprising
(1) allowing a mixture of the compound represented by the general formula (I) and the compound represented by the general formula (II) to react in the presence of:
(i) a reductase or an alcohol dehydrogenase,
(ii) a coenzyme, and
(iii) formic acid or a salt thereof and/or glucose in a buffer solution to convert either the compound represented by the general formula (I) to a compound represented by the general formula (I') or the compound represented by the general formula (II) to a compound represented by the general formula (II'):

[Formula 3]

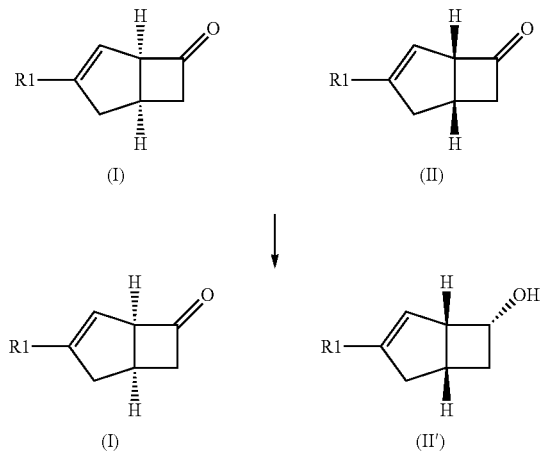

or

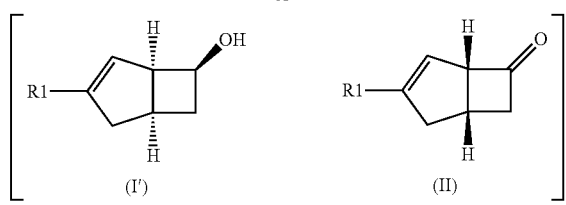

wherein $R^1$: a hydrogen atom or a C1-C6 alkyl group, and then
(2) separating the compound represented by the general formula (I) from the compound represented by the general formula (II') or separating the compound represented by the general formula (II) from the compound represented by the general formula (I') to produce the compound represented by the general formula (I) or the compound represented by the general formula (II).

Preferred aspects of the present invention are as described below.

[2] A method for producing a compound represented by the general formula (I):

[Formula 4]

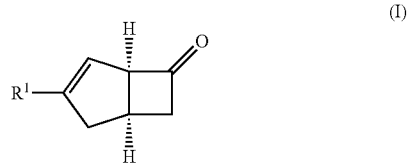

the method comprising
(1) allowing a racemic mixture of the compound represented by the general formula (I) and a compound represented by the general formula (II) to react in the presence of:
(i) a reductase or an alcohol dehydrogenase,
(ii) a coenzyme, and
(iii) formic acid or a salt thereof and/or glucose
in a buffer solution to convert the compound represented by the general formula (II) to a compound represented by the general formula (II'):

[Formula 5]

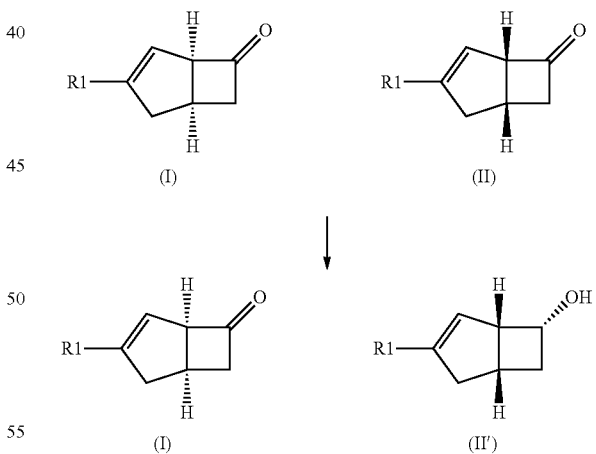

wherein $R^1$: a hydrogen atom or a C1-C6 alkyl group, and then
(2) separating the compound represented by the general formula (I) from the compound represented by the general formula (II') to produce the compound represented by the general formula (I).

[3] The method according to [1] or [2], wherein the reductase or the alcohol dehydrogenase used is E039 (manufactured by Daicel Corp.), and the coenzyme used is nicotinamide adenine dinucleotide ($NAD^+$ or NADH).

[4] The method according to any one of [1] to [3], wherein the step (2) comprises reacting the compound represented by the general formula (I') or the compound represented by the general formula (II') with a cyclic acid anhydride in the presence of a base, followed by the separation.

[5] The method according to any one of [1] to [4], wherein $R^1$ is a hydrogen atom, a methyl group, or an ethyl group.

[6] The method according to any one of [1] to [5], wherein the reaction in the step (1) is performed at a reaction temperature of 20 to 40° C.

[7] The method according to any one of [1] to [6], wherein in the step (1), the reductase or the alcohol dehydrogenase is used in an amount of 4 to 20% by weight with respect to the compound represented by the general formula (I) and/or the compound represented by the general formula (II), and the coenzyme is used in an amount of 0.001 equivalents or lower with respect thereto.

[8] The method according to any one of [1] to [7], wherein the formic acid or the salt thereof is sodium formate.

[9] The method according to any one of [1] to [8], wherein the buffer solution is a phosphate buffer solution, and the phosphate buffer solution has a concentration of 50 mmol or higher.

[10] The method according to any one of [3] to [9], wherein in the step (2), the cyclic acid anhydride is succinic anhydride, maleic anhydride, or phthalic anhydride, and the base is a tertiary amine.

[11] A method for producing a compound represented by the general formula (IV) or a salt thereof, comprising using a compound represented by the general formula (I) produced by a method according to any one of [2] to [10]:

[Formula 6]

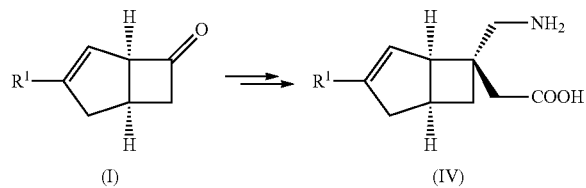

Advantageous Effects of Invention

The present invention is useful for producing an optically active bicyclic γ-amino acid derivative or a pharmacologically acceptable salt thereof, particularly, a compound having activity as an $\alpha_2\delta$ ligand and an intermediate thereof.

The production method of the present invention involves preparing the intermediate as an optically active compound in an earlier step in the production and as such, is efficient.

In addition, a purification step can be performed more efficiently by the reaction of a cyclic acid anhydride with a compound represented by the general formula (II').

DESCRIPTION OF EMBODIMENTS

A C1-C6 alkyl group refers to a linear or branched alkyl group having 1 to 6 carbon atoms and includes, for example, a methyl group, an ethyl group, a propyl group, an isopropyl group, a butyl group, an isobutyl group, a sec-butyl group, a pentyl group, and a hexyl group. A methyl group, an ethyl group, or a propyl group is preferred.

A compound represented by the general formula (I) or the general formula (II) is preferably a compound wherein $R^1$ is a hydrogen atom, a methyl group, or an ethyl group, more preferably a compound wherein $R^1$ is an ethyl group.

[Formula 7]

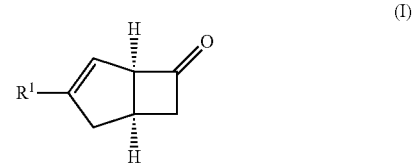

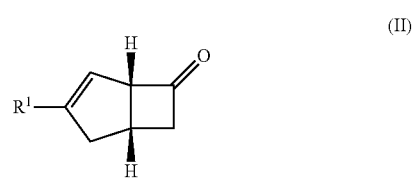

Regarding Step (1)

The reaction temperature is preferably 20 to 40° C., more preferably 20 to 35° C.

The buffer solution used in this step is not particularly limited as long as the buffer solution is usually used in enzymatic reactions. A phosphate buffer solution is preferred. The concentration of the phosphate buffer solution ($K_2HPO_4$.$KH_2PO_4$) is preferably 50 mmol or higher, more preferably 50 to 200 mmol.

Water used in the reaction is usually purified water. Alternatively, tap water may be used.

This reaction is performed using two liquid layers, one of which is composed of the compound represented by the general formula (I) and the compound represented by the general formula (II) as reactive substrates and the other of which is composed of the phosphate buffer solution. The reaction therefore proceeds slowly under weak stirring. Thus, it is important to render the reaction solution homogeneous by moderate stirring.

As for the concentration of the compound represented by the general formula (I) and the compound represented by the general formula (II) as reactive substrates in the reaction solution, the phosphate buffer solution is used in an amount preferably 10 or more times, more preferably 10 to 100 times the volume of the reactive substrates.

The amount of the reductase or the alcohol dehydrogenase used is 4 to 20% by weight, preferably 5 to 10% by weight, with respect to the compound represented by the general formula (I) and compound represented by the general formula (II) as reactive substrates.

The formic acid or the salt thereof used is preferably sodium formate. The sodium formate is used in an amount of preferably 1 to 3 equivalents with respect to the compound represented by the general formula (I) and the compound represented by the general formula (II) as reactive substrates.

The amount of the coenzyme used is preferably 0.0001 to 0.003 equivalents, more preferably 0.0001 to 0.001 equivalents, with respect to the compound represented by the general formula (I) and the compound represented by the general formula (II) as reactive substrates.

A commercially available reductase or alcohol dehydrogenase included in, for example, Chiralscreen OH sold in Daicel Corp. or KRED Screening Kit sold in Codexis, Inc. can be used as the reductase or the alcohol dehydrogenase. The enzyme is preferably E001, E039, E078, catalog No. IC-001 (containing formate dehydrogenase, enzymatic activity: reductase (as oxidative activity) 4.2 U/mg), catalog No. IH-001 (containing formate dehydrogenase, enzymatic activity: reductase (as oxidative activity) 4.0 U/mg), etc. sold in Daicel Corp. E039 is particularly preferred.

Nicotinamide adenine dinucleotide (NAD⁺ or NADH), nicotinamide adenine dinucleotide phosphate (NADP⁺ or NADPH), or the like can be used as the coenzyme. The coenzyme is preferably nicotinamide adenine dinucleotide (NAD⁺ or NADH), for example, catalog No. 308-50446 (β-NAD⁺: β-nicotinamide adenine dinucleotide, oxidized form, manufactured by Oriental Yeast Co., Ltd.) sold by Wako Pure Chemical Industries Ltd.

The buffer solution used is not particularly limited and is, for example, a phosphate buffer solution, preferably a 5 to 200 mmol phosphate buffer solution. The buffer solution is preferably used in a 10- to 20-fold amount (v/w, with respect to the substrates).

More preferred conditions involve adding a 12- to 18-fold amount of a 80 to 150 mmol phosphate buffer solution (v/w, with respect to the substrate concentration), a 0.03- to 0.08-fold amount of a reductase E039 (w/w), 0.0001 to 0.001 equivalents of a coenzyme β-NAD+, and 0.9 to 1.5 equivalents of sodium formate to the reactive substrates, followed by stirring at 20 to 40° C. for 20 to 40 hours.

Further preferred conditions involve adding a 15-fold amount of a 100 mmol phosphate buffer solution (v/w, 6.7% with respect to the substrate concentration), a 0.06-fold amount of E039 (w/w), 0.00025 equivalents of a coenzyme β-NAD+, and 1 equivalent of sodium formate to the reactive substrates, followed by stirring at 25 to 35° C. (standard: 30° C.) for 22 to 25 hours (standard: 24 hours).

Regarding Reaction with Cyclic Acid Anhydride and Separation in Step (2)

The cyclic acid anhydride is preferably succinic anhydride, maleic anhydride, or phthalic anhydride, particularly preferably succinic anhydride.

The base is preferably a general tertiary amine (e.g., triethylamine or pyridine). Particularly preferably, pyridine and a catalytic amount of DMAP (4-dimethylaminopyridine) are used.

The solvent is preferably any aprotic solvent (ethers, esters, hydrocarbons, halogenated hydrocarbons, etc.). Particularly preferably, a mixed solvent of TBME (t-butyl methyl ether) and DMAc (N,N-dimethylacetamide) is used.

The reaction temperature is preferably on the order of 40 to 60° C.

In this step, for example, the compound represented by the general formula (II') is converted to a carboxylic acid compound represented by the general formula (II") through its reaction with the cyclic acid anhydride. As a result, the compound represented by the general formula (I) can be easily separated from the compound represented by the general formula (II") by the usual procedure of separation into aqueous and organic layers under alkaline conditions.

[Formula 8]

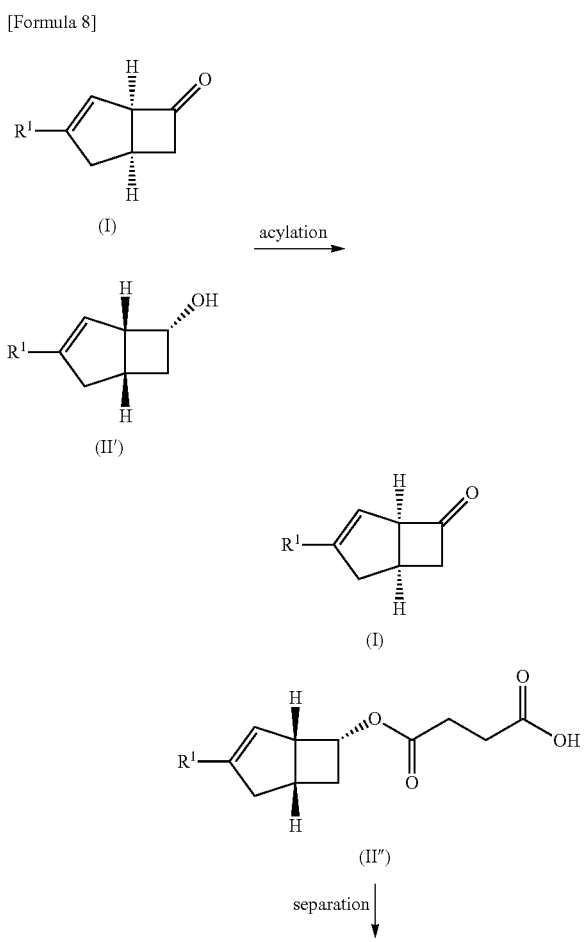

A compound represented by the general formula (IV) or the general formula (IV') can be produced in the same way as in a production method described in Patent Literature 6 (WO 2010/110361) above using the compound represented by the general formula (I) or the compound represented by the general formula (II).

[Formula 9]

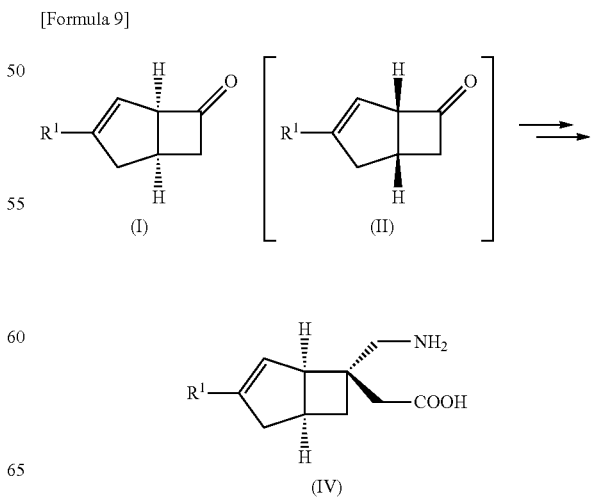

-continued

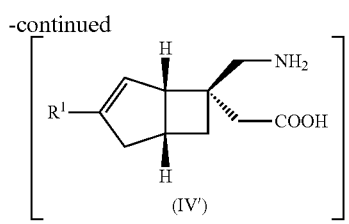

Since compounds represented by the general formula (IV), or the like form salts through reaction with an acid or a base by having amino and carboxyl groups in their structure, a "salt" as used herein refers to these salts.

The compound represented by the general formula (IV), or the like, when left in the air or recrystallized, may associate with adsorbed water through water absorption to form a hydrate. Such hydrates are also encompassed by the salts of the present invention.

The compound represented by the general formula (IV) or a salt thereof exhibits activity as an $\alpha_2\delta$ ligand and affinity for voltage-dependent calcium channel subunit $\alpha_2\delta$ and is useful as an active ingredient in a pharmaceutical composition used for treating and/or preventing pain, central nervous system involvement, and other disorders.

EXAMPLES

Example 1

(1R,5S)-3-Ethylbicyclo[3.2.0]hept-3-en-6-one

[Formula 10]

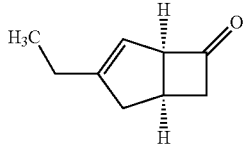

A 0.1 M phosphate buffer solution (pH 7, 1.5 L), sodium formate (50.0 g, 50 wt %), β-NAD⁺ (125 mg, 0.125 wt %, 0.00025 equivalents), and a reductase E039 (6.00 g, 6.0 wt %, manufactured by Daicel Corp.) were added in this order to racemic 3-ethylbicyclo[3.2.0]hept-3-en-6-one (100 g, 0.743 mol).

After stirring at 30° C. for 24 hours, Celite (registered trademark) 535 (20.0 g, 20 wt %) was added to the mixture, followed by filtration. The residue was washed with TBME (800 mL) and combined with the filtrate. The aqueous layer in the filtrate was removed. Then, the organic layer was washed with 20% saline (160 mL).

To this solution, DMAc (200 mL), pyridine (145 g, 2.5 eq.), DMAP (8.97 g, 0.10 eq.), and succinic anhydride (73.5 g, 1.0 eq.) were added in this order, and the mixture was stirred at 60° C. for 8 hours. The reaction mixture was cooled to room temperature and then washed with water (600 mL) to obtain an organic layer. The aqueous layer was subjected to extraction twice with TBME (200 mL for each). The combined organic layers were washed with 2 M hydrochloric acid (1.0 L), then further washed twice with a 5% aqueous sodium bicarbonate solution (1.0 L for each), and concentrated. The concentrated residue was diluted with hexane (500 mL), washed with a 5% aqueous sodium bicarbonate solution (500 mL) and 20% saline (200 mL) in this order, and then concentrated. The residue was distilled (pressure: 2.8 to 3.0 kPa, distillation temperature: 102 to 104° C.) to obtain (1R,5S)-3-ethylbicyclo[3.2.0]hept-3-en-6-one (41.3 g, yield: 41%, 97.7% ee).

<GC Analysis Conditions>

Column: Cyclosil-B (0.25 mm×30 m, DF=0.25 μm)
Flow rate: 1.5 mL/min (He) Split ratio: 1/10
Oven temperature: 130° C. (0-13 min)→230° C. (18-20 min)
Injection port temperature: 230° C. Detector temperature: 230° C.
Retention time: (1R,5S)-3-ethylbicyclo[3.2.0]hept-3-en-6-one (8.2 min) (1S,5R)-3-ethylbicyclo[3.2.0]hept-3-en-6-one (9.5 min) 3-ethylbicyclo[3.2.0]hept-3-en-6-ol (reduced form) (9.2 min)

Example 2

Tert-butyl [(1R,5S,6S)-6-(aminomethyl)-3-ethylbicyclo[3.2.0]hept-3-en-6-yl]acetate D-mandelate

[Formula 11]

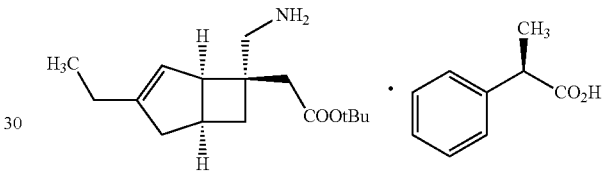

Potassium t-butoxide (8.66 g) was dissolved in tetrahydrofuran (50 mL) under a nitrogen atmosphere, and the solution was then cooled to approximately 5° C. Tert-butyl (dimethoxyphosphoryl)acetate (17.30 g) was added thereto at 15° C. or lower, and the mixture was stirred at 5 to 15° C. for 1 hour. (1R,5S)-3-Ethylbicyclo[3.2.0]hept-3-en-6-one (10.00 g) and tetrahydrofuran (25 mL) were further added thereto, and the mixture was stirred at 5 to 15° C. for 1.5 hours. Potassium t-butoxide (0.90 g) and tert-butyl (dimethoxyphosphoryl)acetate (1.73 g) were further added thereto, and the mixture was stirred for approximately 1 hour. Then, the reaction mixture was separated into aqueous and organic layers by the addition of toluene (85 mL) and water (40 mL). The organic layer was washed twice with water (20 mL) and then concentrated under reduced pressure to obtain tert-butyl [(1R,5S)-3-ethylbicyclo[3.2.0]hept-3-en-6-ylidene]acetate (23.09 g) as a yellow oil.

To tert-butyl [(1R,5S)-3-ethylbicyclo[3.2.0]hept-3-en-6-ylidene]acetate (23.09 g) thus obtained, dimethyl sulfoxide (40 mL), 1,8-diazabicyclo[5.4.0]-7-undecene (22.36 g), and nitromethane (17.93 g) were added under a nitrogen atmosphere, and the mixture was heated with stirring at 60° C. After 5 hours, the heating was stopped, and the reaction mixture was cooled in ice and then separated into aqueous and organic layers by the addition of ethyl acetate (70 mL) and water (80 mL). The organic layer was washed with water (60 mL) and then concentrated under reduced pressure to obtain tert-butyl [(1R,5S,6S)-3-ethyl-6-(nitromethyl)bicyclo[3.2.0]hept-3-en-6-yl]acetate (20.89 g, content: 95.1%) as a red oil (diastereomeric mixture; dr=87/13).

To tert-butyl [(1R,5S)-3-ethyl-6-(nitromethyl)bicyclo[3.2.0]hept-3-en-6-yl]acetate (20.86 g) thus obtained, ethanol (167 mL) and a sponge-nickel catalyst PL-9T (manufactured by Kawaken Fine Chemicals Co., Ltd., 4.28 g, used after washing three times with ethanol) were added under a nitrogen atmosphere, and then, hydrazine monohydrate (13.48 g) was gradually added dropwise. After stirring at 30 to 35° C. for 2 hours, the catalyst was filtered off, and the filtrate was concentrated under reduced pressure to obtain tert-butyl [(1R,5S,6S)-6-(aminomethyl)-3-ethylbicyclo[3.2.0]hept-3-en-6-yl]acetate (22.37 g) as a yellow-orange oil (diastereomeric mixture; dr=88/12).

To tert-butyl [(1R,5S,6S)-6-(aminomethyl)-3-ethylbicyclo[3.2.0]hept-3-en-6-yl]acetate (15.03 g) thus obtained, acetonitrile (300 mL) was added under a nitrogen atmosphere, and the mixture was heated at an internal temperature of 40 to 45° C., followed by the addition of D-mandelic acid (6.07 g). After confirming deposition of crystals, the reaction mixture was stirred at 40 to 45° C. for approximately 1 hour, then gradually cooled to an internal temperature of 0 to 5° C. over approximately 1 hour, and stirred for approximately 1 hour with the temperature maintained. Then, crystals were obtained by filtration, and washed with acetonitrile (60 mL) cooled to 0 to 5° C., and then dried under reduced pressure to obtain white crystals of tert-butyl [(1R,5S,6S)-6-(aminomethyl)-3-ethylbicyclo[3.2.0]hept-3-en-6-yl]acetate D-mandelate (13.22 g) (99.1% de, 99.8% ee, yield from (1R,5S)-3-ethylbicyclo[3.2.0]hept-3-en-6-one: 79%).

The invention claimed is:

1. A method of producing a compound of formula (I):

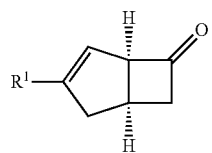
(I)

comprising:
(1) allowing a racemic mixture of the compound of formula (I) and a compound of formula (II)

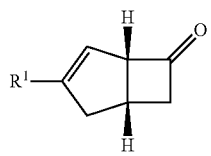
(II)

to react in the presence of:
a reductase or an alcohol dehydrogenase,
a coenzyme, and
a compound selected from formic acid, a salt of formic acid, glucose and a combination of the foregoing,
in a buffer solution to convert the compound of formula (II) to a compound of formula (II'):

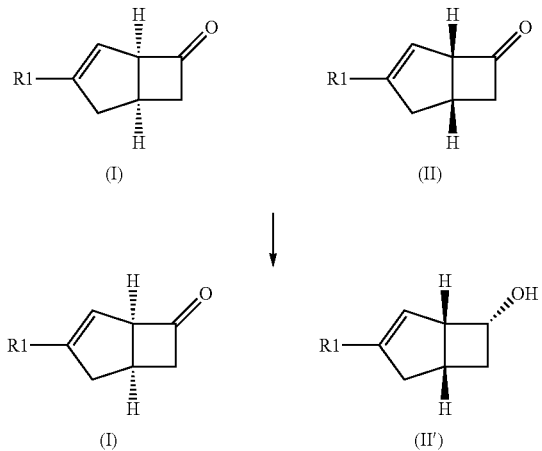

wherein $R^1$ is an ethyl group,
and
(2) separating the compound of formula (I) from the compound of formula (II') to produce the compound of formula (I).

2. The method of claim 1, wherein the reductase or the alcohol dehydrogenase is a formate dehydrogenase, and the coenzyme is $NAD^+$ or NADH.

3. The method of claim 1, wherein the step (2) comprises reacting the compound of formula (II') with a cyclic acid anhydride in the presence of a base, followed by the separation.

4. The method of claim 3, wherein in the step (2), the cyclic acid anhydride is succinic anhydride, maleic anhydride, or phthalic anhydride, and the base is a tertiary amine.

5. The method of claim 1, wherein the reaction in the step (1) is performed at a temperature of 20 to 40° C.

6. The method of claim 1, wherein in the step (1), the reductase or the alcohol dehydrogenase is in an amount of 4 to 20% by weight with respect to the compound of formula (I) or the compound of formula (II), and the coenzyme is in an amount of 0.0001 to 0.001 equivalents with respect to the compound of formula (I) or the compound of formula (II).

7. The method of claim 1, wherein the formic acid or the salt thereof is sodium formate.

8. The method of claim 1, wherein the buffer solution is a phosphate buffer solution, and the phosphate buffer solution has a concentration of 50 to 200 mmol.

* * * * *